United States Patent
McLoughlin et al.

(10) Patent No.: US 7,799,146 B2
(45) Date of Patent: Sep. 21, 2010

(54) APPARATUS AND METHOD OF ULTRASONIC CLEANING AND DISINFECTION

(75) Inventors: Arthur R. McLoughlin, South Australia (AU); Darren M Bates, Queensland (AU); Andrew S. Yap, South Australia (AU); William A. Wright, South Australia (AU)

(73) Assignee: Cavitus Pty Ltd, Crafers (AU)

( * ) Notice: Subject to any disclaimer, the term of this patent is extended or adjusted under 35 U.S.C. 154(b) by 645 days.

(21) Appl. No.: 11/348,732

(22) Filed: Feb. 6, 2006

(65) Prior Publication Data

US 2006/0191424 A1    Aug. 31, 2006

(30) Foreign Application Priority Data

Feb. 8, 2005    (AU) .............................. 2005900531

(51) Int. Cl.
*B08B 9/00* (2006.01)
(52) U.S. Cl. .................................................. 134/166 R
(58) Field of Classification Search ................. 134/1, 134/22.1, 22.11, 166 R, 184; 68/3 SS
See application file for complete search history.

(56) References Cited

U.S. PATENT DOCUMENTS

| | | | | |
|---|---|---|---|---|
| 2,650,872 A | * | 9/1953 | Goldwasser | .................... 8/159 |
| 3,973,760 A | * | 8/1976 | Browning et al. | ............ 366/111 |
| 4,991,609 A | * | 2/1991 | Browning | .................. 134/57 R |
| 5,078,144 A | * | 1/1992 | Sekino et al. | ............... 600/439 |
| 5,531,157 A | | 7/1996 | Probst | |
| 6,432,212 B1 | * | 8/2002 | Hirose et al. | .................... 134/6 |
| 6,799,729 B1 | | 10/2004 | Voic | |

FOREIGN PATENT DOCUMENTS

| | | |
|---|---|---|
| DE | 29608966 | 10/1996 |
| JP | 2-86880 | * 3/1990 |
| WO | WO 2005/007310 | * 1/2005 |
| WO | WO 2005/007310 A1 | 1/2005 |

* cited by examiner

*Primary Examiner*—Michael Kornakov
*Assistant Examiner*—Stephen Ko
(74) *Attorney, Agent, or Firm*—Blakely, Sokoloff Taylor & Zafman LLP

(57) ABSTRACT

An apparatus for and method of disinfecting the interior surfaces of barrels and destroying microorganisms is disclosed. In one embodiment, an ultrasonic apparatus includes a sonotrode encased in a sheath, placed within a bunghole of a barrel. An ultrasonic generator is connected to the sonotrode. The ultrasonic apparatus also includes an ultrasonic transducer connected to the ultrasonic generator and associated with the sonotrode.

16 Claims, 5 Drawing Sheets

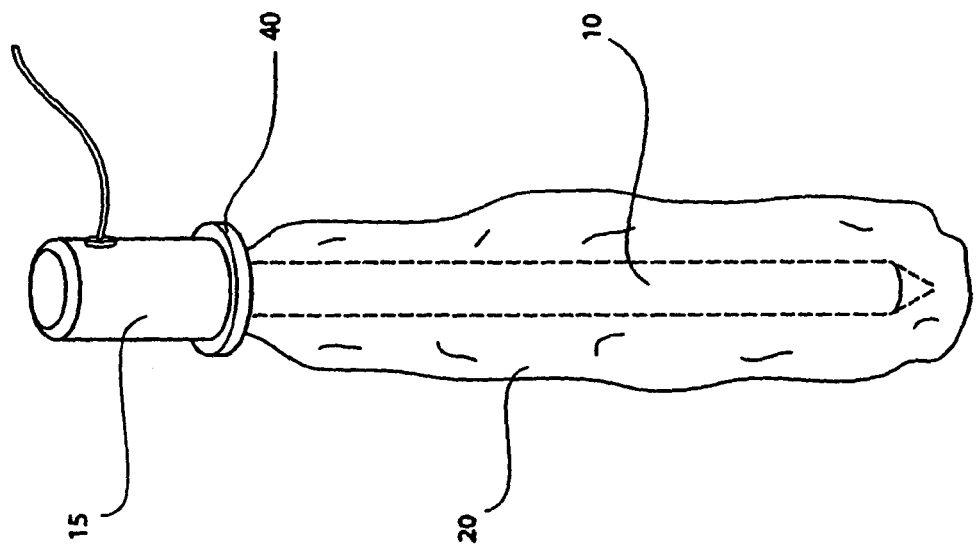

APPARATUS AND METHOD OF ULTRASONIC CLEANING AND DISINFECTION

CROSS-REFERENCE TO OTHER APPLICATIONS

This application claims priority from Australian Patent Application No. 2005900531 filed on Feb. 8, 2005.

FIELD OF THE INVENTION

The present invention relates generally to ultrasonics and, more particularly, to an apparatus and method of ultrasonic disinfection in the presence of heated fluid in the temperature range 25° C. to 95° C. and in particular in the temperature range 30° C. and 60° C.

BACKGROUND OF THE INVENTION

The recycling of wine barrels is common practice within the wine industry. Reusing barrels is one of the ways that wineries can reduce their overheads. This is especially true in large wineries where multiple hundreds of barrels are in circulation at any one time. Barrels have a limited life and are only able to be cleaned a certain number of times. To extend the life of a barrel, it is first used for white wines, cleaned and then used for red wines. The time that the wine spends in a particular barrel depends on the type and quality of the wine that is being produced.

The wood of a new barrel imparts the most flavour into the wine, with the effect being diminished with each re-use of the barrel. Therefore since new barrels are expensive their initial use is normally reserved for premium wines. The third use of a barrel usually doesn't add much flavor to the wine. For this reason many producers manage their barrels carefully, ageing their wine in a mix of new and used barrels to avoid over-oaking the wine. Care however must be taken in the use of older barrels, since the interior can harbor bacteria and yeasts that might contaminate the wine that is to be placed in the cleaned barrel. Such contamination costs the wine industry vast amounts each year in spoilt wine. Furthermore, the winemaker will not know whether a wine has been spoilt until it has spent some time in the barrel.

In order to overcome this problem, the inner surface of the wine barrel is often shaved to remove wine residues. Various apparatuses including cutting routers, planes and rotating wire brushes have been used to remove a small amount of wood off the inner surface of the barrel's staves. The process involves either the dismantling of the barrel or the removal of one end of the barrel. The wood of the interior of the barrel is then shaved to remove residues. Shaving the wood reduces the chance of contaminating the wine that is to be placed in the barrel at a latter time. The method however is not time effective since the barrel must be moved to a location where it can be shaved. Furthermore the inner surface of the barrel must be re-toasted.

Other methods used for decontaminating a barrel involve the use of high-pressure hot or cold water or steam to clean the interior surface of the barrel. A high-pressure water or steam lance is inserted through the bunghole and is manually manipulated or rotated to spray jets of water or steam over the internal surface of the barrel. This loosens the wine residue, tartrates and the like which can then be removed. The detritus can then be drained by the use of a pump or by inverting the barrel.

An alternate method that is used involves inverting the barrel over a cleaning nozzle that sprays high-pressure hot or cold water or steam over the interior surface of the barrel. The advantage of using steam or high-pressure hot water to clean the residue from the interior surface is that it also disinfects the surface. However, both methods of using steam or water are limited because they require the application of the steam or water to occur directly on the inner surface of the barrel. This poses problems especially around the bunghole, as it is difficult to rotate the nozzle to a position where the surface is directly contacted by the steam or water. Furthermore these methods often require a large amount of water and power, as the water needs to be heated.

Throughout this specification, the term sonotrode is used to describe a component that transmits ultrasonic vibrations produced from a transducer to the material to be sonified.

OBJECT OF THE INVENTION

It is an object of the present invention to provide an apparatus for performing ultrasonic activities in which a sonotrode is at least substantially immersed in a first liquid, and the first liquid is separated from a second liquid by a membrane.

It is an object of the present invention to overcome, or at least substantially ameliorate, the disadvantages and shortcomings of the prior art.

Other objects and advantages of the present invention will become apparent from the following description, taken in connection with the accompanying drawings, wherein, by way of illustration and example, an embodiment of the present invention is disclosed.

The present apparatus and method for cleaning and disinfecting wine barrels uses ultrasonics in combination with said heated water to overcome at least some of the aforementioned problems and provides the wine industry with a useful alternative.

Other objects and advantages of the present invention will become apparent from the following description, taken in connection with the accompanying drawings, wherein, by way of illustration and example, an embodiment of the present invention is disclosed.

SUMMARY OF THE INVENTION

According to the present invention there is an ultrasonic apparatus, including a sonotrode that is at least substantially surrounded by a membrane, an ultrasonic generator connected to the sonotrode; and an ultrasonic transducer connected to the ultrasonic generator, such that when in use the sonotrode is placed within the inside of a container, the container containing a first liquid, the sonotrode being at least partially surrounded by a second liquid, the membrane being positioned between the first and second liquids so that the sonotrode is in direct contact with the second liquid and not the first liquid In preference, the membrane is distensible.

In preference, the membrane forms a bladder at least partially surrounding the sonotrode so that when the bladder is filled with the second liquid it expands.

In preference, the membrane has a reinforced region where the membrane comes into contact with the opening of the container so as to provide protection to the membrane when inserted into the container. This then reduces the likelihood of the membrane becoming worn due to wear of the membrane if it should come into contact with the opening of the container.

In preference, there is a conduit for transferring liquid into and out of the membrane.

In preference, the sonotrode is selected from the group consisting of a hollow and solid sonotrodes.

In preference, the conduit is located within the sonotrode.

In preference, the sonotrode is further characterized in that the sides of the sonotrode are profiled to be parallel, concave, or convex.

In preference, the sonotrode includes an end that has an orientation of a plurality of orientations, the plurality of orientation including flat, normal or otherwise to a long axis, concave or convex normal or otherwise to the long axis, and of a symmetrical or asymmetrical reduced or constant section.

In preference, there is an ultrasonic activity sensor adapted to indicate an amount of ultrasonic activity within the container.

In preference, the ultrasonic transducer creates ultrasonic energy at frequencies within a range of 10 kHz to 2000 kHz.

In preference, the membrane is permeable.

In a further aspect of the invention there is described a method for ultrasonic disinfection, comprising placing a first liquid in the temperature range 25° C. to 95° C. and in particular in the temperature range 30° C. and 60° C. in contact with a portion of an inner surface of a container; placing an ultrasonic sonotrode at least substantially surrounded by a membrane, filling said membrane with a volume of a second liquid in the temperature range 5° C. to 50° C. and in particular in the temperature range 5° C. to 25° C., to fill a void volume of the container having an ultrasonic generator connected to the sonotrode, and an ultrasonic transducer connected to the ultrasonic generator such that when in use the sonotrode is in direct contact with the second liquid and not the first liquid, and operating the ultrasonic sonotrode to effect cavitations in the first and second liquids.

In preference, operating the ultrasonic sonotrode comprises operating the ultrasonic sonotrode to induce ultrasonic cavitations within the liquids and disinfects the inner surface of the container.

An apparatus for and method for operating an ultrasound device is disclosed. In one aspect, a sonotrode is at least partially surrounded by a membrane and placed within a container containing a first liquid (L1), such as heated water.

A second liquid (L2), such as water having a temperature of 10° C. to 25° C., is then placed in direct contact with the sonotrode. The membrane thus forms a barrier between the two liquids L1 and L2 so that they are separated. The amount of second liquid added is sufficient so that the membrane becomes expanded to fill any void volume of said partly filled container such that the free water (L1) in the container wets all internal surfaces of the container. An ultrasonic generator is connected to the sonotrode. The ultrasonic apparatus also includes an ultrasonic transducer connected to the ultrasonic generator and associated with the sonotrode.

According to one aspect of the present apparatus and method of ultrasonic activity, the ultrasonic energy emitting shaft, hereinafter referred to as the sonotrode, encased within a bladder, can be introduced into the container through the opening of a partly filled container thereby avoiding the need to dismantle the container. Said bladder is then filled with water and expanded to fill the void volume of said partly filled container such that the free liquid in the barrel wets all internal surfaces of the container. Ultrasonic energy transmits with less propagation losses through cold water than through heated water and the transfer of ultrasonic energy from the sonotrode to the wetted surfaces of the container is enhanced and more effective cavitation occurs at the wetted surfaces of the container when the sonotrode is encased in a bladder containing a volume of liquid, such as water, in the temperature range 5° C. to 50° C. and in particular in the temperature range 5° C. to 25° C., said volume being equivalent to a significant proportion of the void volume of the empty container. The presence of said sheath also serves to reduce the volume of disposable liquid required for the cleaning and disinfection of the barrel interior.

In another embodiment of the present invention, the sonotrode, encased within a bladder, can be introduced into the barrel through the opening of a partly or wholly filled container thereby avoiding the need to dismantle the container. Said bladder is then filled with water. Ultrasonic energy created in the water contained by the non-bladder constructed from a continuous membrane, is transmitted through the bladder wall into the free water contained within the container. It is found that the presence of the bladder serves to, by way of partial internal reflection of the ultrasonic waves generated by the sonotrode, enhance the resultant cavitations cleaning and disinfection effects arising from the ultrasonic energy transmitted into the free water contained within the barrel.

In yet another aspect of the present invention, the sonotrode, encased within a non-expandable, porous sheath, can be introduced into the barrel through the bunghole of a partly or wholly filled barrel thereby avoiding the need to dismantle the wine barrel. Said bladder is then filled with water as the barrel is filled with water. Ultrasonic energy created in the water contained within the bladder, is transmitted through the bladder wall into the free water contained within the container. It is found that the presence of the bladder serves to, by way of partial internal reflection of the ultrasonic waves generated by the sonotrode, creates harmonic frequencies which increase the population density of cavitation bubbles in the water contained within the container and hence enhance the resultant cleaning and disinfection effects arising from the ultrasonic energy transmitted into the free water contained within the container.

In yet a further aspect of the present invention, the sonotrode, complete with an attached rotatable parabolic reflector, can be introduced into the container through the opening of a partly or wholly filled container thereby avoiding the need to dismantle the container. Said rotatable parabolic reflector is of a similar length to that of the longitudinal axis of the sonotrode and is continuously rotated about the longitudinal axis of the sonotrode. Ultrasonic energy created is concentrated by the parabolic reflector and is focused on a limited area of wetted container surface opposite said reflector. It is found that the presence of parabolic reflector serves to enhance the resultant cleaning and disinfection outcomes arising from the ultrasonic energy transmitted into the free water contained within the container.

In yet another embodiment of the present invention, the sonotrode, encased within a bladder, is positioned externally above the opening and introduced into a partially filled container through an opening thereby avoiding the need to dismantle the container. Said bladder is then filled with water in the temperature range 5° C. to 50° C. and in particular in the temperature range 5° C. to 25° C. such that the water within the container and external to the bladder, completely wets all the internal surfaces of the container. Ultrasonic energy created in the water contained within the bladder is transmitted through the bladder wall into the free water contained within the container.

In another aspect of the present invention, an apparatus and method of ultrasonic cleaning and disinfection allows the cleaning and disinfection of a container in situ, without the container having to be moved off site.

In yet a further aspect, chemical disinfectants normally used in the industry to achieve disinfection, such as ozone and sulphur dioxide, are added to the water in the container interiors. The high power ultrasound emitted by the sonotrode interacts synergistically with chemical disinfectants to achieve a satisfactory level of disinfection at markedly reduced concentrations of said chemicals employed.

An apparatus for and method of cleaning and disinfecting the interior surfaces of barrels by destroying microorganisms is disclosed.

In one embodiment, an ultrasonic apparatus includes a sonotrode encased in a bladder, placed within an opening of a container. An ultrasonic generator is connected to the sonotrode. The ultrasonic apparatus also includes an ultrasonic transducer connected to the ultrasonic generator and associated with the sonotrode. The bladder is filled with cool water and the bladder is filled with heated water prior to activating the ultrasonic apparatus.

BRIEF DESCRIPTION OF THE DRAWINGS

The accompanying drawings, which are included as part of the present specification, illustrate the presently preferred embodiment of the present invention and together with the general description given above and the detailed description of the preferred embodiment given below serve to explain and teach the principles of the present invention.

FIG. 4 is a perspective view of the present invention.

DETAILED DESCRIPTION

Figure 1:
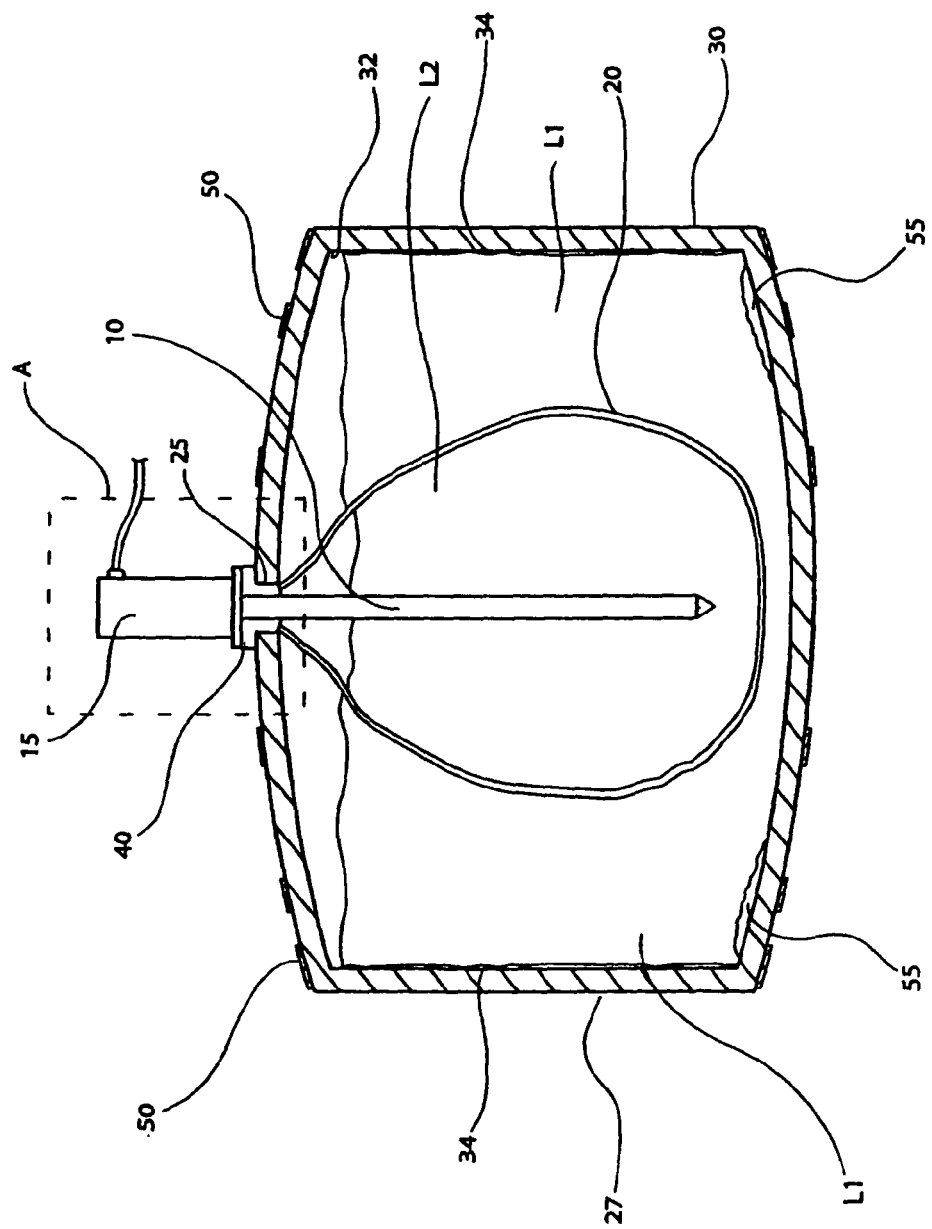
FIG. 1 is a side cut away view of the ultrasonic apparatus in a barrel, according to one aspect of the present invention.

The following detailed description refers to the accompanying drawings. Although the description refers to an exemplary embodiment related to the cleaning of containers and in particular wine containers, other embodiments are possible such as the use of the present ultrasonic apparatus in sonochemistry and other ultrasonic related activities, and changes may be made to the embodiment described herein without departing from the spirit and scope of the invention. For purposes of explanation, specific nomenclature is set forth to provide a thorough understanding of the present invention. However, it will be apparent to one skilled in the art that these specific details are not required in order to practice the present invention.

The practice of recycling wine barrels by way of cleaning is used extensively within the wine industry. However bacterial and yeast contaminations resulting from incomplete cleaning costs the wine industry vast amounts each year in spoilt wine. One of the difficulties faced with wine and liquor container is that the opening of such containers is often restricted. This poses significant problems when such a container is cleaned. Wooden wine barrels are either partially or totally dismantled and the insides of the staves are shaved. Recently high-pressure water or steam has been used to clean such containers. This, however, presents other problems especially in drier areas where winemakers have limited water available.

Additionally a satisfactory level of disinfection within the barrel cannot be achieved by exposing the spoilage microorganisms to power ultrasound in the presence of water at ambient temperatures because the cell walls of said organisms are resistant to disruption even at uneconomically high power levels of ultrasonic energy, at these temperatures.

However, it is found that the use of power ultrasound in the presence of water at temperatures in the range 25° C. to 95° C. and in particular at temperatures in the range 30° C. and 60° C., will kill spoilage microorganisms and yield a satisfactory level of disinfection within the barrel because the cell walls of said organisms are sufficiently weakened at these temperatures to disrupt in the presence of high power ultrasonic energy at said temperatures.

It is also found that because ultrasonic energy transmits with less propagation losses through cold water than through heated water, the transfer of ultrasonic energy from the sonotrode to the wetted surfaces of the barrel is enhanced and more effective cavitation occurs at the wetted surfaces of the barrel when the sonotrode is encased in a sheath or bladder containing a volume of water in the temperature range 5° C. to 50° C. and in particular in the temperature range 5° C. to 25° C., said volume being equivalent to a significant proportion of the void volume of the empty barrel. It of course would be understood by those skilled in this particular art that other liquids may be employed, especially when the container to be cleaned is made from material other than wood. Moreover, it is also appreciated that the liquid inside the bladder or may be different to that inside the container in terms of their chemical and/or physical properties.

The present embodiments therefore use ultrasonics in combination with heated water in the temperature range 25° C. to 95° C. and in particular in the temperature range 30° C. and 60° C., to disinfect and clean wine barrels and like containers with restricted access.

Generally, the wine barrels are disinfected by the use of ultrasonics in the presence of heated water in the temperature range 25° C. to 95° C. and in particular in the temperature range 45° C. and 60° C. This disinfection method works by the action of microscopic cavities collapsing and releasing shock waves. Said shock waves in the presence of heated water in the temperature range 25° C. to 95° C. and in particular in the temperature range 45° C. and 60° C., disrupt the cell walls of the spoilage microorganisms thus killing the organisms. The microscopic cavities are formed by sending sound at high frequencies into a body of heated liquid in the temperature range 25° C. to 95° C. and in particular in the temperature range 45° C. and 60° C., within the barrel.

As illustrated in FIG. 1, the sonotrode 10 of an ultrasonic processor 15 surrounded by a bladder 20, is inserted into the opening 25 of a wine barrel 30. The opening 25 may be in the form of a bunghole or other larger opening, say for example if an end 27 of the wine barrel 30 were to be removed.

In FIG. 1 the ultrasonic sonotrode 10 encased in a bladder 20 is inserted through the opening or bunghole 25 of the wine barrel 30. FIG. 1 shows an ultrasonic processor 15 including a sonotrode 10, an intermediate flange 40, and a generator 45. At least one ultrasonic transducer (not shown) is associated with the sonotrode 10. The total diameter of the sonotrode is less than the diameter of the bunghole 25 of the wine barrel 30. The sonotrode 10 encased in the bladder 20 may be fixed in a single position or able to pivot accordingly. The sonotrode 10 is preferably made from titanium however the reader should understand that the invention is not limited to an ultrasonic processor 15 with titanium sonotrode 10.

As illustrated in FIG. 1 an intermediate flange 40 holds the ultrasonic processor 15 in place once the sonotrode 10 encased in a bladder 20 has been inserted through the bunghole 25. The intermediate flange 40 does not have to produce a perfect seal as the cleaning is only a short-term process and little water will be lost. However, the flange 40 prevents the ultrasonic processor 15 from being dislodged from the bunghole 25 when the barrel 30 is rotated or moved. The average diameter of a bunghole of a standard wine barrel is between 49-50 mm at the outside surface of the barrel and 47-48 mm at the interior surface. Therefore the sonotrode 10 of the ultrasonic processor 15 is less than the smallest diameter of the bunghole 25, according to one embodiment. In alternate embodiments, the sonotrode 10 may be tapered.

In instances where the container to be cleaned has a significantly larger opening then the flange 40 may not be required.

The generator 45 produces an ultrasonic signal that is emitted by the transducer associated with the sonotrode 10, inside the barrel 30. The ultrasonic disinfection method works by the action of microscopic cavities collapsing and releasing shock waves. Said shock waves in the presence of heated water in the temperature range 25° C. to 95° C. and in particular in the temperature range 45° C. and 60° C., disrupt the cell walls of the spoilage microorganisms thus killing the organisms. The microscopic cavities are formed by sending sound at high frequencies into a body of liquid that is in contact with the surface 32 to be disinfected. In the present embodiment, the microscopic cavities form on the interior surface of the wooden staves 50 of the wine barrel 30. The shock waves produced by the collapse of the cavities loosen the wine residue, tartrates, and the like 34 on the inside walls 32 of the barrel 30. This detritus 55 can then be drained by the use of a pump or by inverting the barrel 30 and allowing the detritus 55 to drain out through the bunghole 25.

To avoid the creation of fixed position standing waves, the water L1 within the wine barrel 30 may be agitated. This can be accomplished by either agitating the water using a pump (not shown) or by allowing the sonotrode 10 encased in a bladder 20 of the ultrasonic processor 15 to rotate or pivot.

Figure 2:
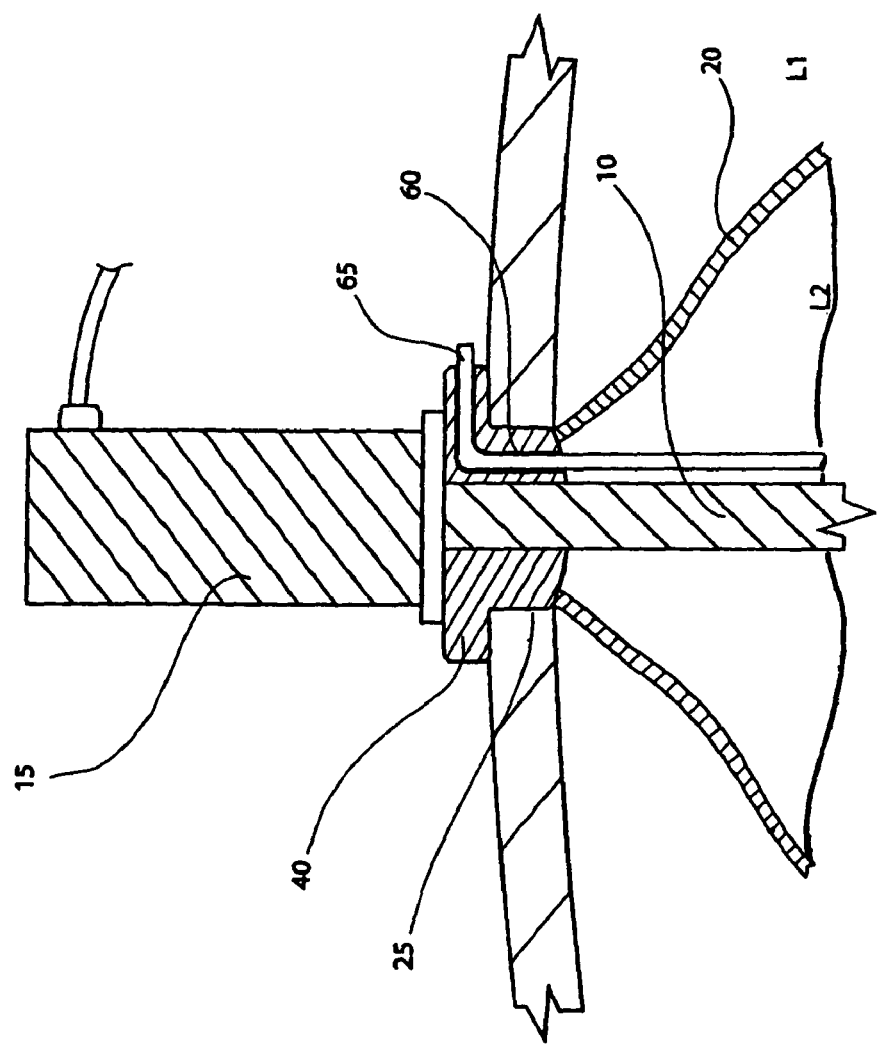
FIG. 2 is a close up side cut away view of section A of the ultrasonic apparatus in a barrel shown in FIG. 1.
Figure 3A:
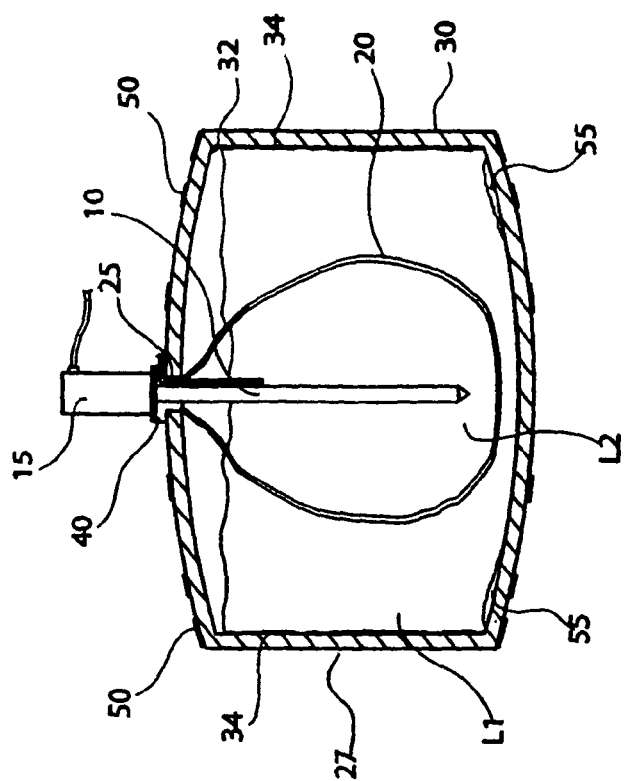
FIG. 3A is a side cut away view of the present invention prior to the introduction of the second liquid.
Figure 3B:
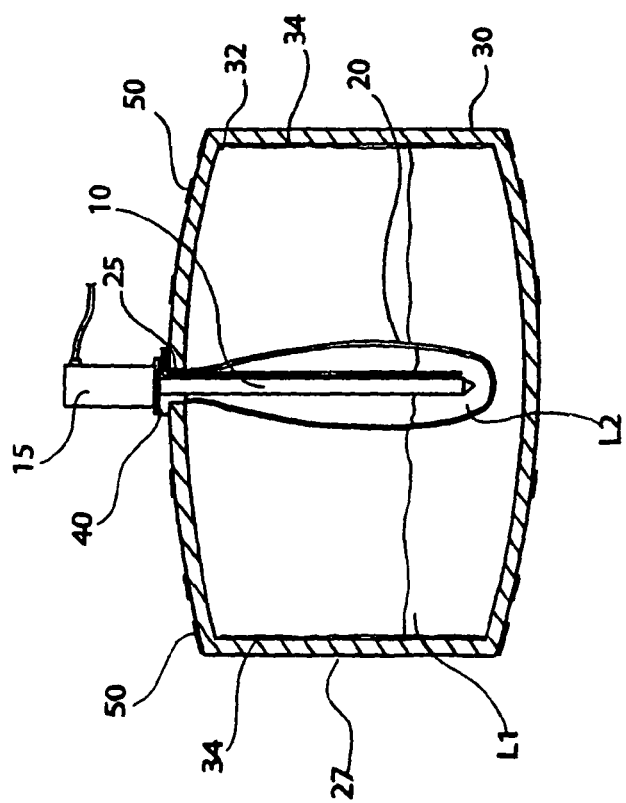
FIG. 3B is a side cut away view of the present invention as shown in FIG. 3A after the addition of the second liquid.

FIG. 2 illustrates a side cut away view of a wine barrel 30 with the flange 40 in place. The flange 40 has an aperture 60 located thereon to allow for the insertion of a conduit 65 there through so that water L2 can be pumped in or out of the bladder 20 as appropriate. The conduit 65 is constructed from a pliable material so that it does not interfere with the propagation of waves through the liquid L2 in the bladder 20. The intermediate flange 40 is adapted to allow movement of the sonotrode 10 by applying pressure to the sonotrode 10. As further illustrated in FIGS. 3A and 3B, the wine barrel 30 does not need to be completely filled with water L1. In the present example, as shown in FIG. 3A, the barrel 30 is only half filled with water L1 in the temperature range 25° C. to 95° C. and in particular in the temperature range 45° C. and 60° C. Water L2, in the temperature range 5° C. to 50° C. and in particular in the temperature range 5° C. to 25° C. is then inserted into the bladder 20 through the conduit 65 and as the bladder 20 expands the level of liquid L2 rises in the barrel 30, as shown in FIG. 3B. As mentioned previously, the use of cooler water L2 allows for greater efficiency in the productions of cavitations in the liquid L2 and therefore increasing the efficiency in the productions of cavitations in L1. This then in combination with the greater temperature of the liquid L1 results is a dramatically enhanced cleaning effect on the inside of the barrel 30. As the reader would now appreciate reducing the amount of water L1 used is a significant advantage especially where disinfection is performed in areas having restricted water access.

Figure 5:
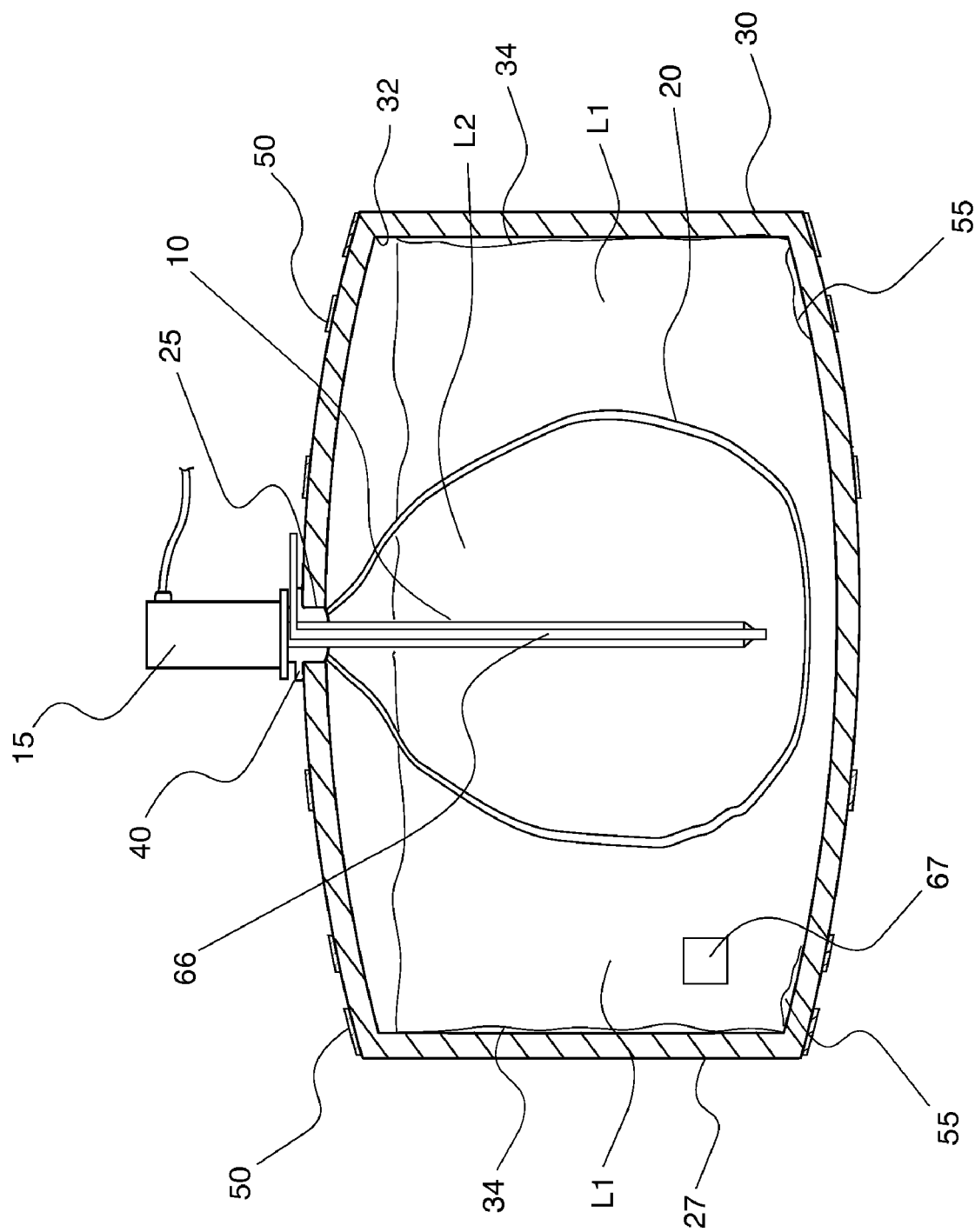
FIG. 5 is a side cut away view of the ultrasonic apparatus in a barrel, according to one aspect of the present invention.

In another embodiment of the invention, as illustrated in FIG. 5, the conduit (66) is located within the hollow sonotrode (10), allowing for the transfer of liquid (L2) into and out of the bladder (20).

As illustrated in FIG. 5, the location and specification of the ultrasonic activity sensor (67) can be locate anywhere within the barrel (30), as would be appreciated by a person skilled in the art, to monitor the amount of ultrasonic activity within the barrel (30).

Additionally, due to the reduced need for warmer water L1, overall energy consumption is also reduced.

In another embodiment of the invention, a pump (not shown) can be used to recycle the water through a filter, thus limiting the amount of water L1 required for the disinfection process.

Since the wine barrel is only half filled with liquid L1 the barrel 30 must be rotated on at least one axis, preferably the horizontal axis according to one embodiment, so that all surfaces of the barrel come in contact with the liquid L1 and ultrasonic cavitations. Rollers that are commonly used in the wine industry to rotate barrels 30 would be sufficient for this task. It should however be understood that the invention is not limited to half filled barrels. The barrel may be completely or partially filled with liquid that is then filtered and recycled for use in cleaning other barrels.

It should be understood by the skilled person in the art that the cables and pipes associated with the embodiments of the present invention are of a sufficient length to enable barrels to be disinfected in situ, even when the barrels are at a distance from power or water sources. Furthermore, the ultrasonic processor 15 can also be located on a boom to enable the user to manipulate the processor 15 with ease, even when the barrels 30 are stacked or on rollers high above the ground.

The use of ultrasonics in the presence of heated water in the temperature range 25° C. to 95° C. and in particular in the temperature range 45° C. and 60° C. is a cost effective way to disinfect wine barrels 30. The present apparatus and method avoids the need to completely dismantle the wine barrel 30 or even to remove one end of the barrel 30. The ability of ultrasonics in the presence of heated water in the temperature range 25° C. to 95° C. and in particular in the temperature range 45° C. and 60° C. to disinfect the interior surface of the wine barrel 30 also means that the chances of cross contamination from bacteria and yeast are reduced. Furthermore, the ease with which the present invention can be used in conjunction with currently available equipment, such as barrel rollers, increases the likelihood of this technique being used by wineries. Added to these advantages are the reduction in disinfection time and the fact that less water is required for the disinfection process.

Depending on the strength of the cavitation energy and/or the size of the barrel it may be advantageous to be able to internally move the sonotrode 10. The movement may either be one or two-dimensional either defining an arc within the barrel 30 and pivoting end to end or rotating in a circle within the wine barrel 30. Both movements have the effect of alternating the distance between the surface area to be disinfected and the sonotrode 10. The pivoting or rotational motion may be accomplished by well-known mechanical means such as an electric motor, a motor operating on water pressure or by manual means with the ultrasonic apparatus 15 mounted on a hinge.

As discussed above, the application of ultrasonic energy to barrels may remove tartrate crystals that are encrusted on to the surface 32 of oak wood barrels and suspend them, along with other residues (referred to as "lees") in the bottom of the barrels in which wine has been stored for periods of time. As a consequence of the tartrate removal, there will be better transfer of oak flavor to the wine. This ensures that the interior surface of an oak barrel is completely devoid of undesirable organics and inorganic matter which can be detrimental to wine quality. The suspended substances are easily removed during the disinfection process. Disinfection with ultrasonics reduces heating costs and the uses of chemicals. There is less loss of wood compounds using high power ultrasonics as compared to high pressure hot or cold water sprays. As a result, a barrel's life can be extended, thus reducing the cost of replacing barrels.

High power ultrasonics in the presence of heated water in the temperature range 25° C. to 95° C. and in particular in the temperature range 30° C. and 60° C. kills the spoilage yeast *Brettanomyces*. This organism and other spoilage yeasts, and bacteria are found in the pores and cracks of oak wood wine barrels, especially around the inner surface at the interior of the barrel. In the embodiment of a wood barrel this is the location where wine residue is found at the interior surface layers of the wood. The ability of high power ultrasonic energy in the presence of heated water in the temperature range 25° C. to 95° C. and in particular in the temperature range 45° C. and 60° C. to heat and disinfect liquid and solid substances permits inactivation of organisms found on the interior staves surfaces of oak barrels present and to the depth of up to 8 mm or more. Ultrasonic energy disinfection avoids or minimizes the use of chemicals, such as sulphur dioxide and ozone.

If the container is only partially full of fluid, it is necessary to move the fluid to wet other portions of the inner surface of the container. The fluid may be moved by expanding the bladder 20, according to one embodiment. After cleaning, the ultrasonic sonotrode 10 encased in the bladder 20 is removed from the barrel 30. This can be done both mechanically or physically. Once the container is disinfected, any debris within the container is removed and the fluid is drained from the container.

The present apparatus and method avoid spoilt wine caused by contamination, improve transfer of oak flavor to the wine through reduced tartrate deposits in the barrels, avoid the loss of oak flavor through existing washing methods, lower barrel costs by avoiding replacing barrels spoilt by contamination, lower barrel costs by extending the usable life of barrels, lower labor costs for cleaning operations, lower water costs, avoid the of use of chemicals, and lower water heating costs.

Further advantages and improvements may very well be made to the present invention without deviating from its scope. Although the present invention has been described with respect to specific examples and subsystems, it will be apparent to those of ordinary skill in the art that the invention is not limited to these specific examples or subsystems but extends to other embodiments as well. The present invention includes all of these other embodiments as specified in the claims that follow.

The claims defining the invention are as follows:

1. An ultrasonic apparatus, including:
    a sonotrode shaft at least substantially surrounded by a distensible bladder to be placed within the inside of a container, the distensible bladder having an inside surface and an outside surface;
    an ultrasonic generator connected to the sonotrode shaft; and
    an ultrasonic transducer connected to the ultrasonic generator and associated with the sonotrode shaft;
    the container containing a first liquid, the distensible bladder containing a second liquid, the sonotrode shaft being at least partially surrounded by the second liquid, the distensible bladder being positioned between the first and second liquids, the inside surface of the distensible bladder being in contact with the second liquid and the outside surface of the distensible bladder being in contact with the first liquid, so that the sonotrode shaft is in direct contact with the second liquid and not the first liquid.

2. The ultrasonic apparatus of claim 1, further characterized in that there is a conduit for transferring the second liquid into and out of the distensible bladder.

3. The ultrasonic apparatus of claim 2, further characterized in that the conduit is located within the sonotrode shaft.

4. The ultrasonic apparatus of claim 2, wherein the sonotrode shaft is further characterized in that sides of the sonotrode shaft are profiled to be parallel, concave, or convex.

5. The ultrasonic apparatus of claim 4, wherein the ultrasonic transducer creates ultrasonic energy at frequencies within a range of 10 kHz to 2000 kHz.

6. The ultrasonic apparatus of claim 5, wherein the ultrasonic transducer creates ultrasonic energy at frequencies within a range of 10 kHz to 40 kHz.

7. The ultrasonic apparatus of claim 6, further comprising an ultrasonic activity sensor adapted to indicate an amount of ultrasonic activity within the container.

8. An ultrasonic apparatus, including:
    a sonotrode shaft to be disposed within the inside of a container to be partially filled with a first liquid;
    a distensible bladder configured to be filled with a second liquid when disposed within the inside of the container, wherein the distensible bladder at least partially surrounds the sonotrode, wherein, when the distensible bladder is filled with the second liquid, an inside surface of the distensible bladder is in contact with the second liquid, an outside surface of the distensible bladder is in contact with the first liquid, and the sonotrode shaft is in direct contact with the second liquid and not the first liquid;
    an ultrasonic generator connected to the sonotrode shaft; and
    an ultrasonic transducer connected to the ultrasonic generator and associated with the sonotrode shaft.

9. The ultrasonic apparatus of claim 8, wherein the distensible bladder is configured to expand, when filled with the second liquid, to fill a void volume of said partially filled container such that the first liquid in the container wets substantially all internal surfaces of the container.

10. The ultrasonic apparatus of claim 8, further comprising a conduit to transfer the second liquid into and out of the distensible bladder.

11. The ultrasonic apparatus of claim 8, wherein the ultrasonic transducer creates ultrasonic energy at frequencies within a range of 10 kHz to 2000 kHz.

12. The ultrasonic apparatus of claim 8, wherein the first liquid is in the temperature range of 30° C. to 60° C. and the second liquid is in the temperature range of 5° C. to 25° C.

13. An ultrasonic apparatus, including:
    a distensible bladder;
    a sonotrode shaft encased within the distensible bladder to be disposed within an opening of a container partially filled with a first liquid, wherein the distensible bladder is configured to be filled with a second liquid when disposed within the container, wherein the distensible bladder is configured to expand, when filled with the second liquid, to fill a void volume of said partially filled container such that the first liquid in the container wets substantially all internal surfaces of the container, and wherein, when filled with the second liquid, an inside surface of the distensible bladder is in contact with the second liquid, an outside surface of the distensible bladder is in contact with the first liquid, and the sonotrode shaft is in direct contact with the second liquid and not the first liquid;

an ultrasonic generator connected to the sonotrode shaft; and an ultrasonic transducer connected to the ultrasonic generator and associated with the sonotrode shaft.

14. The ultrasonic apparatus of claim 13, further comprising a conduit to transfer the second liquid into and out of the distensible bladder.

15. The ultrasonic apparatus of claim 13, wherein the ultrasonic transducer creates ultrasonic energy at frequencies within a range of 10 kHz to 2000 kHz.

16. The ultrasonic apparatus of claim 13, wherein the first liquid is in the temperature range of 30° C. to 60° C. and the second liquid is in the temperature range of 5° C. to 25° C.

* * * * *